(12) United States Patent
Schnyder et al.

(10) Patent No.: US 7,528,266 B2
(45) Date of Patent: May 5, 2009

(54) PROCESS FOR THE PREPARATION OF 7-SUBSTITUTED 3-ALKYL-3H-ISOBENZOFURAN-1-ONE DERIVATIVES

(75) Inventors: Anita Schnyder, Allschwil (CH); Marco Passafaro, Stein (CH); Thomas Rapold, Wallbach (DE)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 11/874,965

(22) Filed: Oct. 19, 2007

(65) Prior Publication Data

US 2008/0097111 A1 Apr. 24, 2008

Related U.S. Application Data

(63) Continuation of application No. 10/478,020, filed as application No. PCT/EP02/05572 on May 21, 2002, now Pat. No. 7,307,175.

(30) Foreign Application Priority Data

May 22, 2001 (CH) ....................... 954/01

(51) Int. Cl.
*C07D 307/20* (2006.01)
(52) U.S. Cl. ..................... 549/307; 549/310
(58) Field of Classification Search .......... 549/307, 549/310
See application file for complete search history.

(56) References Cited

FOREIGN PATENT DOCUMENTS

| DE | 1112529 | 8/1961 |
|---|---|---|
| DE | 2060063 | 6/1971 |
| WO | 9619443 | 6/1996 |

OTHER PUBLICATIONS

Nagira Kazuhiko et al.: Journal of Organic Chemistry, vol. 45, No. 12, 1980, pp. 2365-2368.
Drozd et al.: Journal of Organic Chemistry USSR (English Translation), vol. 9, 1973, p. 2564.
Mongin F. et al.: "Reagent-Modulated Optional Site Selectivities: The Metalation of o-, m- and p-Halobenzotrifluorides", Tetrahedron Letters, Elsevier Science Publishers, Amsterdam, NL, vol. 37, No. 16, Apr. 15, 1996, pp. 2767-2770.
Ino, A. et al.: "Total Synthesis of the Antimycoplasma Antibiotic Micacocidin", Tetrahedron Letters, Elsevier Science Publishers, Amsterdam, NL, vol. 39, No. 32, May 21, 1998, pp. 3509-3512.
Lüthy, C. et al.: "7-(4,6-Demethoxypyrimidinyl)oxy- and -thiophthalides as novel herbicides: Part 1. CGA 279 233: a new grass-killer for rice", Pest Management Science, Elsevier, Barking, GB, vol. 57, Mar. 16, 2001, pp. 205-224.
Bunnett, J.F. et al: "Steric Acceleration of the Lactonization of 2-(Hydroxymethyl) Benzoic Acids", Journal of The American Chemical Society, American Chemical Society, Washington, D.C., vol. 87, No. 10, May 1965, pp. 2214-2220.
Soucy, D. et al.: "On the Regioselectivity of Mehtal Hydride Reductions of 3-Substituted Phthalic Anhydrides", Journal of Organic Chemistry, American Chemical Society, Easton, US, vol. 52, 1987, pp. 129-134.
Kayser, M. M.: "The Internal steric push-effect: its consequences on the reactivity of carbonyl functions in 3-substituted phthalic anyhdrides;" CA 111:38768 (1989).
Epsztajn, Jan: "Application of organolithium and related reagents in substitution sequence of secondary chlorobenzamides;" Abstract of Monatshefte fuer Chemie (1992), 123 (12), pp. 1125-1134.

*Primary Examiner*—Patricia L Morris
(74) *Attorney, Agent, or Firm*—Rebecca A. Howard

(57) ABSTRACT

The present invention relates to a first compound having the formula

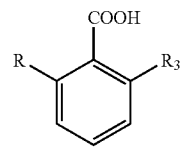

wherein R is halogen, $R_1S(O)_n$ or $(R_1)_2NC(X)O$; $R_1$ is $C_1$-$C_8$alkyl, $C_1$-$C_8$haloalkyl, aryl-$C_1$-$C_8$-alkyl or aryl; n is 0, 1, 2 or 3; X is O or S; and $R_3$ is $C_2$-$C_5$alkyl or $C_1$-$C_5$haloalkyl, or a salt thereof. The present invention is also directed to a second compound having the formula

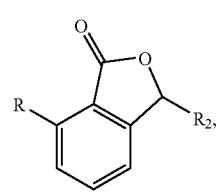

(I)

wherein R is fluorine, bromine, iodine, $R_1S(O)_n$ or $(R_1)_2NC(X)O$; $R_1$ is $C_1$-$C_8$alkyl, $C_1$-$C_8$-haloalkyl, aryl-$C_1$-$C_8$alkyl or aryl; n is 0, 1, 2 or 3; X is O or S; and $R_2$ is hydrogen, $C_1$-$C_4$alkyl or $C_1$-$C_4$haloalkyl, with the proviso that $R_1$ is different from $C_1$-$C_8$ alkyl or aryl if X is S, R is different from iodine if $R_2$ is methyl, and R is different from fluorine, bromine or iodine if $R_2$ is hydrogen.

1 Claim, No Drawings

PROCESS FOR THE PREPARATION OF 7-SUBSTITUTED 3-ALKYL-3H-ISOBENZOFURAN-1-ONE DERIVATIVES

This application is a continuation of application Ser. No. 10/478,020 filed Apr. 7, 2004, now U.S. Pat. No. 7,307,175 which is the National Stage of International Application No. PCT/EP02/05572, filed May 21, 2002, which claims the benefit of Swiss Application No. 954/01, filed May 22, 2001.

The present invention relates to a novel process for the preparation of 7-substituted 3-alkyl-3H-isobenzofuran-1-one derivatives, to their use as intermediates in the preparation of byproduct-free 7-thio-3H-isobenzofuran-1-one derivatives, and to their use as intermediates in the preparation of herbicidal 7-[(4,6-dimethoxy-pyrimidin-2-yl)thio]-3-methyl-3H-isobenzo-furan-1-one.

WO 91/05781 describes a process for the preparation of 7-thio-3-methyl-3H-isobenzofuran-1-one. According to that process, that compound is obtained by rearrangement in three steps starting from 7-hydroxy-3-methyl-3H-isobenzofuran-1-one according to Kwart-Newmann via the 7-(N,N-dimethylthiocarbamoyl)oxy-3-methyl-3H-isobenzofuran-1-one derivative with heating at about 170-200° C. to the 7-(N,N-dimethylcarbamoyl)thio-3-methyl-3H-isobenzofuran-1-one intermediate and is then subjected to alkaline hydrolysis. Since the starting material 7-hydroxy-3-methyl-3H-isobenzofuran-1-one also has to be prepared by a multistep process, that process for the preparation of 7-thio-3-methyl-3H-isobenzofuran-1-one is troublesome and unsuitable for commercial synthesis.

In a further process, starting from 3-nitrophthalic acid the target compound 7-thio-3-methyl-3H-isobenzofuran-1-one is obtained in four reaction steps in a yield of about 60%.

The latter reaction sequence consists of introducing a methyl group using methylmagnesium bromide or malonic acid, reducing a nitro group and a carbonyl group, and then diazotising the resulting 7-amino-3-methyl-3H-isobenzofuran-1-one in the presence of sodium hydrogen sulfide.

Pest Manag Sci. 57, 205-224 (2001) describes further synthesis processes for the preparation of 7-thio-3-methyl-3H-isobenzofuran-1-one (compound of formula Xc in Figure 7 on page 211) in which undesired disulfide byproducts (compounds of formula Xc' in Figure 7) are substantially excluded, e.g. by reduction and simultaneous ring-closure of 2-acetyl-6-nitrobenzoic acid with Raney nickel, diazotisation of the 7-amino-3-methylphthalide (compound of formula XXa) obtained in a crude yield of 89.8%, and subsequent thiol formation by treatment of the corresponding diazonium salt with an alkaline potassium xanthogenate solution in a crude yield of 87.5% over the last two reaction steps.

That process too is unsatisfactory in terms of volumetric and chemical yields. In addition, the use of xanthogenates as source of sulfur for the thiol formation gives rise to volatile, unpleasant-smelling, toxic, sulfur-containing waste products, such as e.g. COS, $CS_2$ and $H_2S$. Moreover, individual reaction steps, such as e.g. the reduction of 3-nitrophthalic acid derivatives to the corresponding amines (formation of hydroxylamine byproducts), have a significant thermal safety risk (TMR (='time to maximum rate')<2 hours). From the standpoint of industrial-scale preparation processes, these aspects are problematic especially in ecological terms and in respect of process safety.

Monatsh. Chem. 123(12), 1125-1134 (1992) describes the preparation of 7-chlorophthalides methyl- or phenyl-substituted in the 3-position by ortho-lithiation of 3-chlorobenzanilides with n-butyllithium, reaction with electrophiles e.g. acetaldehyde, for the preparation of 7-chloro-3-methyl-phthalides, and subsequent acid-catalysed cyclisation. As described above in Pest Manag Sci. 57, 205-224, such 7-chloro-3H-isobenzofuran-1-ones can be converted by treatment with an excess of alkylmercaptides, e.g. sodium methyl- or ethyl-mercaptide, at temperatures of about 100-130° C. in N,N-dimethylformamide to the desired 7-mercapto-3H-isobenzofuran-1-ones by way of a 7-alkylmercapto-3H-isobenzofuran-1-one intermediate. That process too is unsuitable for industrial-scale processes because of the yield, process safety and the formation of unpleasant-smelling dialkylsulfides and is also uneconomical owing to the cost of the reagent n-butyllithium.

Tetrahedron Lett. 36(39), 7089-7092 (1995) and J. Chem. Soc., Perkin Trans. I, 1997, 787-793 describe the oxidative, free-radical-forming, photochemical preparation of lactones at room temperature starting from o-alkyl aromatic carboxylic acids in the presence of [bis(tri-fluoroacetoxy)iodo]benzene and iodine (phenyl-I(O(O)CCF$_3$)$_2$/I$_2$) by way of a hypoiodite species in an organic solvent, such as dichloromethane, and irradiation with a high-pressure mercury vapour lamp in moderate to good yields (from 5 to 90%, based on the starting compound) of the desired lactone, and Tetrahedron Asym. 8, 3765-3774 (1997) describes the preparation of 3-alkylphthalide derivatives starting from o-alkyl aromatic carboxylic acids as biocatalysed benzylic oxidation and lactonisation using microorganisms, such as e.g. *Pseudomonas putida*. Neither synthesis process can be carried out on an industrial scale.

Chem. Ber. 38, 3981-3985 (1905) describes a synthesis variant for the preparation of phthalide derivatives starting from aromatic ortho-aldehydro acids by means of nucleophilic addition using Grignard reagents with the formation of the corresponding alcohol derivatives and subsequent lactonisation of the same.

J. Org. Chem. 51, 3849-3858 (1986) and J. Organomet. Chem. 231, 79-90 (1982) describe a further synthesis variant for 3-methylphthalides by the reduction and lactonisation of 2-methylketonecarboxylic acids using sodium borohydride and ruthenium-triphenyl-phosphine complex and hydrogen ($RuCl_2(PPh_3)_3/H_2$), respectively, in a quantitative yield, and a yield of 51%, respectively.

Tetrahedron Lett. 28(43), 5175-5176 (1987), J. Chem. Soc. Perkin Trans II, 1983, 595-601, Ind. J. Chem. Sect. B 24, 1202-1203 (1985) and Bull. Acad. Sci. USSR Div. Chem. Sci. (Engl. Transl.) 31(10), 2041-2046 (1982) describe the preparation of γ- and δ-lactones from alkanecarboxylic acids by oxidation with oxygen-containing compounds, such as e.g. 2,3-dichloro-5,6-dicyano-1,4-benzoquinone (DDQ) or sodium persulfate ($Na_2S_2O_8$), in the presence of catalytic amounts of copper(II) chloride or nickel(II) chloride, or cerium(IV) ammonium nitrate ($Ce(NH_4)_2(NO_3)_6/HNO_3$) in a yield of 10-35%.

Tetrahedron Lett. 29(1), 85-88 (1988) describes the preparation of γ-lactones from γ-arylbutyric acids via halogenation with bromine in the presence of the free-radical initiator α,α'-azoisobutyronitrile in carbon tetrachloride in a yield of 53%.

J. Org. Chem. 45, 2365-2368 (1980) describes the palladium(0)-catalysed carbonylation of isolated methyl-, methoxy-, halo- and nitro-substituted arenediazonium tetrafluoroborates in acetonitrile in the presence of sodium acetate and carbon monoxide in yields of from 28 to 86%, and J. Chem. Soc., Perkin Trans. I, 1998, 407-410 describes the palladium (II)-catalysed carbonylation of isolated bisarenediazonium tetrafluoroborate salts in methanol at room temperature and normal pressure in yields of from 76 to 93%, based on the diazonium salt.

WO 96/19443 discloses a process for the preparation of aromatic o-sulfo-carboxylic acids by means of diazotisation of the corresponding aniline-2-sulfonic acids and subsequent palladium(II)-catalysed carbonylation of the diazonium salt formed, with or without isolation of that diazonium salt.

Whilst the preparation of sulfides by the reaction of halides with mercaptides, xanthates, thiourea, alkali metal sulfides or alkali metal disulfides (the latter being prepared in situ from alkali metal sulfides and sulfur) are well-documented standard processes, as described e.g. in J. Org. Chem. 56, 3728-3729 (1991), J. Am. Chem. Soc. 68, 498 (1946), Gazz. Chim. Ital. 110, 301-303 (1980), Org. Synth., Coll. Vol. III, 86-87 and Chem. Pharm. Bull. 33, 5184-5189 (1985), they are all unsuitable for industrial-scale batches, because:

a) the reagents used are too expensive, such as e.g. the use of sodium borohydride for the reductive working-up of disulfide derivatives, b) the resulting product yields and product purities are unsatisfactory for industrial-scale preparation processes, c) the amount of di- and poly-sulfides formed is too great, and d) the reproducibility cannot be guaranteed.

The problem of the present invention is to overcome those disadvantages and provide a technically simpler process suitable for industrial-scale processes that is associated with little outlay in terms of apparatus.

It has now been found, surprisingly, that 3-alkyl-3H-isobenzofuran-1-one derivatives substituted specifically in the 7-position can readily be prepared with high product yield, product purity and selectivity, in an economically and ecologically especially advantageous manner, avoiding the disadvantages of the processes described above, from inexpensive and readily accessible starting compounds, such as e.g. aniline derivatives, using technically simple, reproducible and safe process conditions by way of only three or four reaction steps, by diazotising 2,6-disubstituted aniline derivatives, carbonylating the resulting diazonium salt in the presence of catalysts and cyclising the resulting benzoic acid derivative in the presence of a halogenating agent and a free-radical initiator to form the corresponding lactone derivative. That lactone derivative is then used in a further, fourth reaction step for a nucleophilic aromatic substitution reaction with sulfides and a subsequent, specific purification step at a controlled pH range for the preparation of byproduct-free 7-thio-3H-isobenzofuran-1-one, which can be used directly e.g. for the preparation of herbicides according to EP-B-0 447 506. In that process, careful attention is given to the critical factors and crucial reaction parameters in all the reaction steps including working-up, such as e.g. the choice of solvents, acids, bases and buffer systems, the water content in the reaction mixture, the pH range, the reaction temperature, the charging procedure for the palladium complex, pressure and reaction time.

The present invention accordingly relates to a process for the preparation of 7-substituted 3-alkyl-3H-isobenzofuran-1-ones of formula I

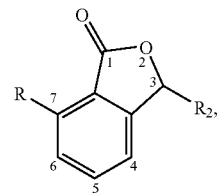

(I)

wherein

R is halogen, $R_1O$, $R_1S(O)_n$ or $(R_1)_2NC(X)O$;

$R_1$ is $C_1$-$C_8$alkyl, aryl-$C_1$-$C_8$alkyl, $C_1$-$C_8$haloalkyl or aryl;

n is 0, 1, 2 or 3;

X is O or S; and $R_2$ is hydrogen, $C_1$-$C_4$alkyl or $C_1$-$C_4$haloalkyl, in which process, in a solvent, (1) an aniline derivative of formula IV

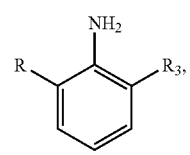

(IV)

wherein

R is as defined above, and $R_3$ is $C_1$-$C_5$alkyl or $C_1$-$C_5$haloalkyl, is diazotised in the presence of a mineral acid to form the corresponding diazonium salt of formula II

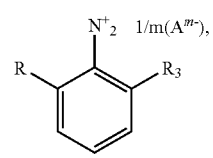

(II)

wherein

R and $R_3$ are as defined above, $A^{m-}$ is an anion such as e.g. $PF_6^-$, $BF_4^-$, $HSO_4^-$, $SO_4^{2-}$, $CH_3(C_6H_4)SO_3^-$, $CH_3SO_3^-$ or $(Zn(II)Cl_3)^-$, and m is 1 or 2, (2) the resulting diazonium salt of formula II is carbonylated in the presence of a catalyst, CO and optionally a buffer, to form a benzoic acid derivative of formula III

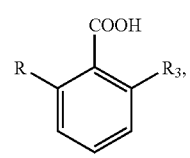

(III)

wherein

R and $R_3$ are as defined above, and (3) the benzoic acid derivative of formula III is then subjected to benzylic lactonisation in the ortho-position alkyl chain $R_3$ in the presence of a free-radical initiator and a halogenating agent.

The compounds of formula I prepared according to the invention are used as starting compounds in the preparation of compounds of formula Ia

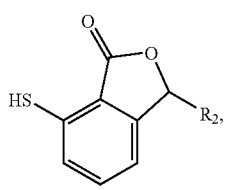

(Ia)

wherein $R_2$ is as defined for formula I, by reacting a compound of formula I

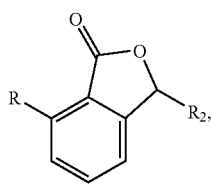

(I)

wherein R is halogen, $R_1SO_2$ or $(R_1)_2NC(X)O$; and X, $R_1$ and $R_2$ are as defined for formula I, with the reagent of formula X $$M_2S_q \quad\quad (X),$$

wherein M is an alkali metal or hydrogen, and q is 1, 2 or a fractional number from 1 to 7, with the proviso that at least one M is an alkali metal (halogen-sulfide exchange; Reaction scheme 3).

The compounds of formulae I and Ia may be in the form of optical isomers and mixtures of isomers depending on the substituents $R/R_1$ and/or $R_2$. Unless enantiomerically pure starting materials are used, the compounds of formulae I and Ia in the processes described above are generally obtained in the form of racemates or diastereoisomeric mixtures, which can optionally be separated on the basis of physicochemical properties according to known methods, such as e.g. fractional crystallisation after salt formation with optically pure bases or metal complexes or by chromatographic processes, such as e.g. high pressure liquid chromatography (HPLC) on acetylcellulose.

In the present invention, the compounds of formulae I and Ia are to be understood as including both the enriched and optically pure forms of the stereoisomers in question and the racemates or diastereoisomers. Where there is no specific reference to the individual optical antipodes, the racemic mixtures under the given formula are to be understood as being those obtained in the preparation process according to the invention.

The present invention includes also the salts that can be formed by the compounds of formulae Ia and III.

For example, owing to their acidity, compounds of formulae Ia and III can readily be converted in the presence of bases (proton acceptors) into the corresponding salts (e.g. with metal ions or ammonium cations). Any customary proton acceptor can be used as base. Such salts are, for example, alkali metal salts, such as e.g. sodium and potassium salts; alkaline earth metal salts, such as e.g. calcium and magnesium salts; ammonium salts, that is to say unsubstituted ammonium salts and mono- or poly-substituted ammonium salts, such as e.g. triethylammonium and methylammonium salts, or salts with other organic bases or other cations, such as e.g. sulfonium or phosphonium cations. Sulfonium cations are, for example, tri($C_1$-$C_4$alkyl)sulfonium cations, which can be obtained from the corresponding alkali metal salts e.g. by conversion into different salts using, for example, a cation exchanger.

Of the alkali metal hydroxides and alkaline earth metal hydroxides as salt formers, special mention may be made, for example, of the hydroxides of lithium, sodium, potassium, magnesium and calcium, but especially those of sodium and potassium. Suitable ammonium salt formers are described, for example, in WO 97/41112.

Examples of amines suitable for ammonium salt formation that come into consideration are ammonia and also primary, secondary and tertiary $C_1$-$C_{18}$alkylamines, and heterocyclic amines. Especially suitable are, for example, trimethylamine, triethylamine, tri-n-propylamine, triisopropylamine, triisobutylamine, pyridine, 5-ethyl-2-methylpyridine and morpholine. More especially suitable are trimethylamine and triethylamine.

In the above definitions, halogen is to be understood as being fluorine, chlorine, bromine or iodine, preferably fluorine, chlorine or bromine.

The alkyl groups appearing in the substituent definitions are, for example, methyl, ethyl, n-propyl, isopropyl, n-butyl, sec-butyl, isobutyl and tert-butyl, and also the pentyl, hexyl, heptyl and octyl isomers.

Haloalkyl groups preferably have a chain length of from 1 to 6 carbon atoms. Haloalkyl is, for example, fluoromethyl, difluoromethyl, difluorochloromethyl, trifluoromethyl, chloromethyl, dichloromethyl, dichlorofluoromethyl, trichloromethyl, 2,2,2-trifluoroethyl, 2-fluoroethyl, 2-chloroethyl, 2,2-difluoroethyl, 2,2-dichloroethyl, 2,2,2-trichloroethyl or pentafluoroethyl, preferably trichloromethyl, difluoromethyl, difluorochloromethyl, trifluoromethyl or dichlorofluoromethyl.

Aryl in the definition of the radical $R_1$ is α- or β-naphthyl, especially phenyl, it being possible for those aromatic rings to carry one or more identical or different substituents, such as e.g. halogen, nitro, cyano, $C_1$-$C_4$alkoxy, $C_1$-$C_4$haloalkoxy, $C_1$-$C_4$alkyl and $C_1$-$C_4$haloalkyl. The same applies also to arylalkyl in the definition of the radical $R_1$.

Corresponding meanings can be assigned also to the substituents in composite definitions of R, such as e.g. alkoxy, haloalkoxy, arylalkyl, aryloxy, arylthio, arylsulfonyl, alkylthio, alkylsulfinyl, alkylsulfonyl, alkylsulfonyloxy, haloalkylthio, haloalkylsulfinyl, haloalkylsulfonyl, haloalkylsulfonyloxy, arylalkylthio, arylalkylsulfinyl and arylalkylsulfonyl.

$A^{m-}$ in the diazonium salt of formula II denotes a mono-(m=1) or di-valent (m=2) anion and according to the definition includes e.g. $PF_6^-$, $BF_4^-$, $HSO_4^-$, $SO_4^{2-}$, $CH_3(C_6H_4)SO_3^-$, $CH_3SO_3^-$ and $(Zn(II)Cl_3)^-$, preferably $PF_6^-$ and $BF_4^-$.

The reagent of formula X, $M_2S_q$, is, when both M are alkali metals and q is 1, an alkali metal sulfide, such as e.g. sodium sulfide ($Na_2S$), potassium sulfide ($K_2S$), lithium sulfide ($Li_2S$) or sodium potassium sulfide (NaKS); when one M is an alkali metal and the second M is hydrogen and q is 1, the reagent of formula X is an alkali metal hydrosulfide, such as e.g. sodium hydrosulfide (NaHS) or potassium hydrosulfide (KHS); when both M are alkali metals and q is 2, the reagent of formula X is an alkali metal disulfide, such as e.g. sodium disulfide ($Na_2S_2$), potassium disulfide ($K_2S_2$) or sodium potassium disulfide ($NaKS_2$), and finally when one M is an alkali metal and the second M is hydrogen and q is 2, the reagent of formula X is an alkali metal hydrodisulfide, such as e.g. sodium hydrodisulfide ($NaHS_2$) or potassium hydrodisulfide ($KHS_2$). For higher values of q, the reagent $M_2S_q$ of formula X denotes compounds such as, for example, $Na_2S_4$ or mixtures prepared in situ from lower alkali metal sulfides and sulfur. The definition of $M_2S_q$ also includes mixtures of lower and higher alkali metal sulfides. The nucleophilic species are then e.g. $NaS^-$, $HS^-$, $NaS_2^-$ and $HS_2^-$.

The process according to the invention is especially suitable for the preparation of compounds of formula I wherein R is chlorine or bromine, especially chlorine.

The process according to the invention is also especially suitable for the preparation of compounds of formula I wherein $R_2$ is $CH_3$.

The process according to the invention is also especially suitable for the preparation of compounds of formula I wherein R is chlorine and $R_2$ is $CH_3$.

The preparation of compounds of formula I by way of three reaction steps (Steps (1), (2) and (3)) and the use thereof in a derivatisation step by means of a nucleophilic aromatic substitution reaction with the reagent of formula X $M_2S_q$ (X) (reaction step 4, halogen-sulfide exchange) to form compounds of formula Ia will be explained in greater detail in the following Reaction schemes 1, 2 and 3.

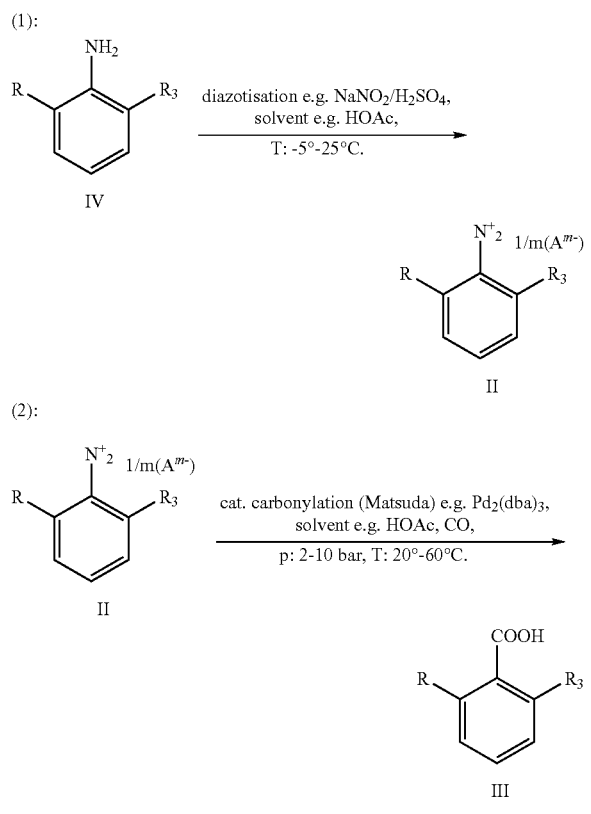

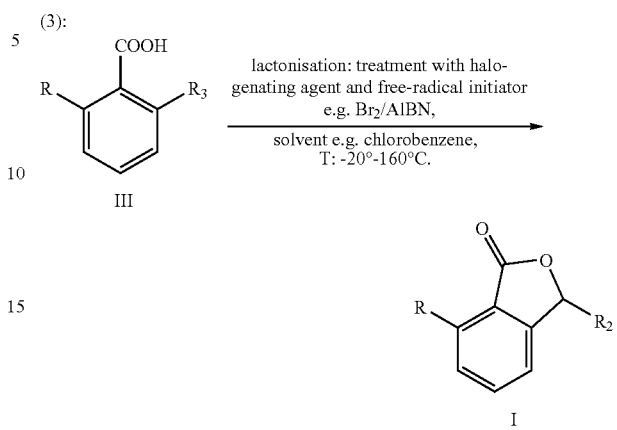

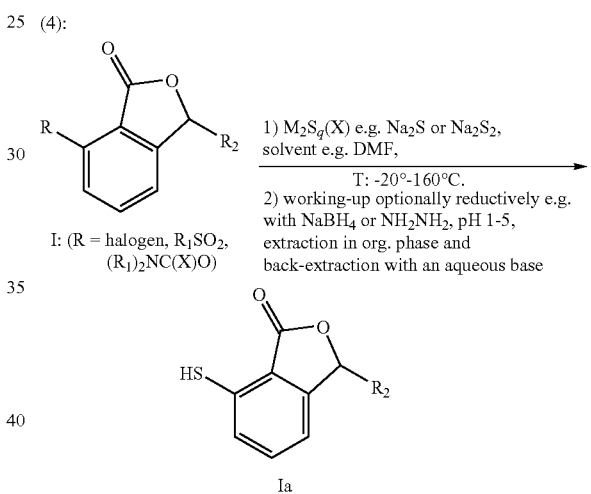

In the first Step (1) in Reaction scheme 1, the diazotisation of the aniline derivative of formula IV is carried out advantageously in a solvent and in the presence of a 20 to 120% excess of a mineral acid, based on the diazotisation reagent, at reaction temperatures in the range of from −5° to 25° C.

As diazotisation reagent there may be used the customary nitrites, such as, for example, alkali metal nitrites, dinitrogen trioxide ($N_2O_3$) or organic nitrites, preferably sodium nitrite, potassium nitrite, $N_2O_3$, tert-butyl nitrite or pentyl nitrite in equivalent amounts or in a slight excess of from 3 to 10% molar equivalents, based on the aniline derivative of formula IV.

Suitable solvents for the diazotisation in Step (1) are $C_1$-$C_4$-carboxylic acids, nitriles, ethers, amides, carbonates, alcohols or water, or mixtures thereof, for example acetic acid, propionic acid, acetonitrile, tetrahydrofuran, dioxane, N,N-dimethylformamide (DMF), N,N-dimethylacetamide (DMA), 1-methyl-2-pyrrolidone (NMP), 1,3-dimethyl-2-imidazolidinone (DMI), propylene carbonate, isoamyl alcohol, n-pentanol, isopropanol, n-propanol, tert-butanol, n-butanol, ethanol, methanol or water, or mixtures thereof. Preference is given to acetic acid, acetonitrile, alcohols and water.

Suitable mineral acids for the diazotisation reaction in Step (1) are preferably sulfuric acid, hydrochloric acid, nitric acid and hydrobromic acid.

The catalysts that come into consideration for the carbonylation of the diazonium salts of formula II in Step (2) (Matsuda carbonylation, Reaction scheme 1) are generally palladium(II) and palladium(0) complexes. Examples of such palladium complexes are palladium(II) dihalides, palladium (II) acetate, palladium(II) sulfate, palladium(II) acetylacetonate, bis-hydridopalladium(II) tetrahalides ($H_2PdCl_4$), bis (alkali metal)palladium(II) tetrahalides, cis,cis-1,5-cyclooctadiene-palladium(II) dihalides, bis(acetonitrile)- and bis(benzonitrile)-palladium(II) dihalides, bis(dibenzylideneacetone)palladium(0) ($Pd_2(dba)_3$), $[Pd(\eta_3-C_3H_5)Cl]_2$, $[Pd(\eta_3-Me-C_3H_4)Cl]_2$, $[Pd(\eta_3-C_3H_5)(acac)]_2$, bis (triphenylphosphine)palladium(II) dihalides and tetrakis (triphenylphosphine)palladium(II) dihalides.

The palladium complexes are prepared ex situ or optionally, in the case of ligand-carrying complexes, such as e.g. triphenylphosphinepalladium(II) complexes, also in situ.

Examples of preferred palladium(0) and palladium(II) catalysts prepared ex situ or in situ are $PdCl_2$, $PdBr_2$, $H_2PdCl_4$ (in the form of a solution in hydrochloric acid), $Na_2[PdCl_4]$, $Li_2[PdCl_4]$, $K_2[PdCl_4]$, $Pd(acac)_2$, $PdCl_2(COD)$ ($=PdCl_2$ (cis,cis-1,5-cyclooctadiene)), $PdCl_2(AcCN)_2$, $PdCl_2(PhCN)_2$, $PdCl_2(PPh_3)_2$, $PdCl_2(PPh_3)_4$ and $Pd(PPh_3)_4$.

Such palladium complexes are known and have been described many times in the literature, such as e.g. in J. Am. Chem. Soc. 121, 4369-4378 (1999), EP-A-0 564 406, EP-A-0 646 590 and 'Palladium Reagents and Catalysts', Editor J. Tsuji, John Wiley & Sons, 1995.

The palladium catalysts are used in an amount of from 0.1 to 5.0 mol %, preferably from 0.25 to 1.00 mol %, based on the compound of formula II.

Suitable solvents for the carbonylation in Step (2) are the same as those listed for the diazotisation in Step (1). Generally, directly before the carbonylation reaction, from 0 to 10 equivalents of water, based on the compound of formula IV, are metered in or an excess of water is reduced using carboxylic acid anhydrides, such as e.g. acetic anhydride (Examples P2 and P3).

The palladium-catalysed carbonylation reaction of the diazonium salt of formula II in Step (2) is carried out at a CO pressure of from 1 to 100 bar and at reaction temperatures of from −20° to 60° C., preferably in a pressurised vessel (autoclave).

The two Steps (1) and (2), the diazotisation and carbonylation in Reaction scheme 1, can be carried out, in principle, according to two different variants:

a) as a two-step reaction with isolation of the intermediately formed, stable diazonium salt of formula II

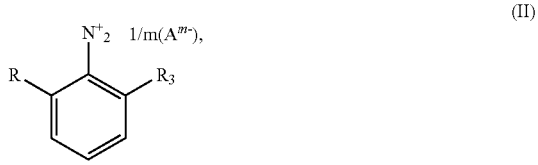
(II)

wherein R, $R_3$, $A^{m-}$ and m are as defined for formula I, or b) preferably as a single-step reaction without isolation of the intermediately formed diazonium salt of formula II

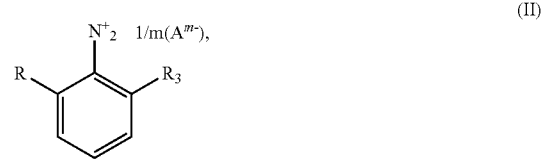
(II)

wherein R, $R_3$, $A^{m-}$ and m are as defined for formula I, with the result that the diazotisation of the aniline derivative of formula IV and the palladium-catalysed carbonylation reaction of the compound of formula II in Steps (1) and (2) are carried out as a continuous process, that is in the same reaction vessel and solvent system as a one-pot reaction.

When selecting one of the two variants a) or b), in addition to considering the stability of the diazonium salt of formula II, the reactants present in the reaction mixture must also be taken into account and must be matched according to the process variant in question in order to avoid possible secondary reactions and thus a reduction in yield. Critical factors are, for example, the selection of the solvent or solvent mixture, of the nitrite reagent as potential catalyst poison and of the mineral acid, e.g. sulfuric acid as opposed to hydrochloric acid, and the buffering of excess mineral acid, for example with acetates, the water content in the reaction mixture, and the nature of the palladium catalyst and its charging procedure, especially the sequence of the addition of CO and the metering of the palladium complex into the reaction mixture. In addition, the reaction parameters, such as e.g. the reaction temperature and the CO pressure in the system, may be critical to the manner in which each reaction proceeds.

Accordingly, prior to the catalytic carbonylation of the diazonium salt of formula II in Step (2) the mineral acid in the reaction mixture is advantageously buffered with a buffer system, preferably using an alkali metal acetate, for example sodium acetate.

Once the diazotisation is complete, excess nitrite reagent present in the reaction mixture is destroyed in customary manner known to the person skilled in the art, for example by adding sulfamic acid (Examples P2 and P3) until nitrite is no longer detectable (nitrite detection using KI paper moistened with 1N aqueous hydrochloric acid solution) and the reaction mixture so treated is prepared for the subsequent palladium-catalysed carbonylation step, which is preferably carried out in the same reaction vessel.

In the case of the two-step variant a), with isolation of the diazonium salt of formula II, the following aqueous base systems, for example, are suitable for the subsequent carbonylation reaction: alkali metal, alkaline earth metal and ammonium salts of acetates, propionates, butyrates, benzoates and stearates, and of carbonates, for example lithium, sodium, potassium, calcium, barium and ammonium acetate, propionate and benzoate, and lithium, sodium, potassium, calcium, barium, magnesium, ammonium and ($C_1$-$C_{18}$alkyl)$_3$NH salts of carbonates.

In an especially preferred variant of Steps (1) and (2) according to the invention, the diazotisation of the aniline derivative of formula IV (Step (1)) is carried out using an equivalent amount of sodium nitrite in the presence of a 25% excess of sulfuric acid, based on the nitrite, and acetic acid as solvent, and the subsequent palladium-catalysed carbonylation reaction (Step (2)) is carried out using $Pd_2(dba)_3 \cdot CHCl_3$ at a CO pressure of from 2 to 10 bar and a reaction temperature of from 20° to 60° C. in the same reaction vessel as a one-pot reaction.

In Step (3) in Reaction scheme 2, the treatment with the halogenating reagent and subsequent or simultaneous ring-closure reaction (lactonisation) of the benzoic acid derivative of formula III are advantageously carried out using halogen, preferably chlorine or bromine, using hypohalite, preferably hypochlorite or hypobromite, or using sulfuryl halide, preferably sulfuryl chloride or sulfuryl bromide, in a solvent, such as e.g. a chlorinated hydrocarbon, a $C_1$-$C_4$carboxylic acid or water, or a mixture thereof, and in the presence of a free-radical initiator, such as e.g. α,α'-azoisobutyronitrile or benzoyl peroxide.

The halogenating reagent is advantageously used in an amount of from 1 to 2 molar equivalents, based on the benzoic acid derivative of formula III.

The solvents especially suitable for Step (3) are, for example, chlorinated hydrocarbons, for example tetrachloroethylene, chloroform, dichloromethane, chlorobenzene and dichlorobenzene, carboxylic acids, for example acetic acid or propionic acid, or water, or mixtures thereof, the reaction temperature being from −20° to 160° C. and the reaction pressure being from 1 to 100 bar.

In an especially preferred variant of Step (3) according to the invention, the treatment with the halogenating reagent and the ring-closure reaction of the compound of formula III are carried out with from 1 to 1.3 molar equivalents of bromine, based on the compound of formula III, in chlorobenzene at reaction temperatures of from 80° to 100° C. and at normal pressure in the presence of α,α'-azoisobutyronitrile as free-radical initiator.

For good selectivity and in order to carry out the reaction in Step (3) efficiently, the choice of the solvent, the amount of halogenating reagent and of free-radical initiator and the purity of the starting compound of formula II, and the reaction parameters, such as temperature and duration of the reaction, are critical in order as far as possible to suppress over-oxidation and the formation of halides, such as e.g. phenyl nuclear halides and alkyl halides ($R_2$). Excess halogenating and oxidising agents can be rendered inactive in the course of a working-up process, for example using an alkali metal thiosulfate, for example using sodium thiosulfate (Example P4).

The yields of isolated product of formula I in all three Steps (1), (2) and (3) are generally >70% of theory (depending on the solvent and acid used, the optimum water content, the charging procedure for the palladium catalyst, the nature and amount of halide and purity of the starting materials) with the final product having a purity of >90%.

The starting compounds of formula IV in Reaction scheme 1 are known e.g. from DE-A-2 405 479 and Ann. Chem. 424, 255 (1921).

All the reagents used, such as diazotisation agents, palladium(II) and palladium(0) catalysts, phosphine ligands and free-radical initiators, are also known or can be prepared according to known processes.

The compounds of formula III

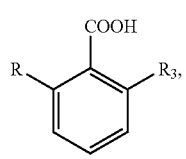
(III)

wherein R is halogen, $R_1S(O)_n$ or $(R_1)_2NC(X)O$; $R_1$ is $C_1$-$C_8$alkyl, $C_1$-$C_8$haloalkyl, aryl-$C_1$-$C_8$-alkyl or aryl; n is 0, 1, 2 or 3; X is O or S; and $R_3$ is $C_2$-$C_5$alkyl or $C_1$-$C_5$haloalkyl, and salts thereof are novel. They make a significant contribution in structural terms to the preparation of the lactones of formulae I and Ia and have been developed especially for the process according to the invention.

Preferred compounds of formula III are those wherein R is halogen or $R_1S(O)_2$ and $R_3$ is ethyl.

The compounds of formula I

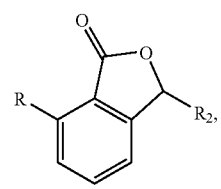
(I)

wherein R is fluorine, bromine, iodine, $R_1S(O)_n$ or $(R_1)_2NC(X)O$; $R_1$ is $C_1$-$C_8$alkyl, $C_1$-$C_8$-haloalkyl, aryl-$C_1$-$C_8$alkyl or aryl; n is 0, 1, 2 or 3; X is O or S; and $R_2$ is hydrogen, $C_1$-$C_4$alkyl or $C_1$-$C_4$haloalkyl, are also novel. They make a substantial contribution in structural terms to the preparation of the lactones of formula Ia and have been developed especially for the use according to the invention.

Preferred compounds of formula I are those wherein R is bromine or $R_1SO_2$ and $R_2$ is methyl. The present invention accordingly relates also to the compounds of formulae I and III.

The present invention accordingly relates also to the use of compounds of formula I in the preparation of 7-thio-3H-isobenzofuran-1-one derivatives of formula Ia

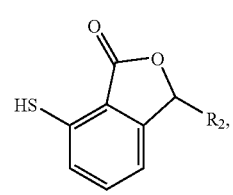
(Ia)

wherein $R_2$ is hydrogen, $C_1$-$C_4$alkyl or $C_1$-$C_4$haloalkyl, wherein a compound of formula I

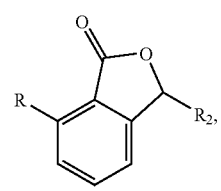
(I)

wherein R is halogen, $R_1SO_2$ or $(R_1)_2NC(X)O$; X is O or S; $R_1$ is $C_1$-$C_8$alkyl, aryl-$C_1$-$C_8$haloalkyl or aryl; and $R_2$ is as defined above, is reacted at elevated reaction temperature in the presence of sulfur in a nucleophilic aromatic substitution reaction with an alkali metal sulfide, disulfide or polysulfide of formula X $$M_2S_q \qquad (X),$$

wherein M is an alkali metal or hydrogen, and q is 1, 2 or a fractional number from 1 to 7, with the proviso that at least one M is an alkali metal (halogen-sulfide exchange; Reaction scheme 3), and optionally, when a reagent of formula X wherein q>1 is used, is worked-up reductively and, after the reaction mixture has been rendered acidic, the desired target compound of formula Ia is isolated therefrom and optionally re-isolated in the form of the salt using a strongly basic aqueous solution.

As alkali metal sulfides or disulfides of formula X for the nucleophilic aromatic substitution reaction (halogen-sulfide exchange) in the compound of formula I, it is possible to use, for example, sodium sulfide ($Na_2S$), potassium sulfide ($K_2S$), lithium sulfide ($Li_2S$), sodium potassium sulfide (NaKS), sodium disulfide ($Na_2S_2$), sodium potassium disulfide ($NaKS_2$), and also alkali metal hydrosulfides and alkali metal hydrodisulfides, for example sodium hydrosulfide (NaHS), potassium hydrosulfide (KHS) and sodium hydrodisulfide ($NaHS_2$) (Reaction scheme 3), the disulfides preferably being prepared in situ in a solvent, such as e.g. an amide, for example DMF, from elemental sulfur and an alkali metal sulfide, e.g. sodium sulfide, analogously to the manner described, e.g. in Gazz. Chim. Ital. 110, 301 (1980), J. Am. Chem. Soc. 68, 498 (1946) and Chem. Pharm. Bull. 33, 5184 (1985).

The alkali metal sulfides and disulfides of formula X are advantageously used in equimolar amounts or in an excess of from 2 to 50 mol %, based on the compound of formula I.

After adjustment of the pH range of the reaction mixture to the acid range, preferably to the pH range of from 1 to 5, the desired compound of formula Ia can be isolated, optionally after reductive working-up when q is 2 in the compound of formula X that is used (disulfides), and then optionally re-isolated from the organic phase using a strongly basic aqueous solution (Example P6).

Solvents suitable for the nucleophilic aromatic substitution of the compounds of formula I are generally, for example, alcohols, ethers, aromatic hydrocarbons, sulfoxides, amides, esters or water, or mixtures thereof, for example ethanol, propanol, butanol, 2-methoxyethanol, tetrahydrofuran, dioxane, toluene, dimethyl sulfoxide, N,N-dimethylformamide, 1-methyl-2-pyrrolidone, N,N-dimethylacetamide, ethyl acetate or water, or mixtures thereof.

The nucleophilic aromatic substitution of the compounds of formula I is carried out at a reaction temperature of from −20° to 160° C., preferably from 80° to 100° C., and at normal pressure (1 bar) or in a sealed system at an elevated pressure of from 1.1 to 100 bar.

Optionally, it is possible additionally to add phase transfer catalysts, especially quaternary ammonium salts, such as e.g. tetraalkylammonium halides, for example tetrabutylammonium chloride and tricaprylomethylammonium chloride (aliquat), as solubilisers between the dissolved starting material of formula I and the disulfide, which may have been prepared in situ, which has the effect of accelerating the reaction. Further phase transfer catalysts suitable for the above nucleophilic aromatic substitution reaction are described, for example, in Synthesis 1973, 441-456 and in Angew. Chem., Int. Ed. Engl. 13, 170-179 (1974). Such phase transfer catalysts are used in amounts of from 0.1 to 10 mol %, especially from 0.5 to 5 mol %, based on the compound of formula Ia.

A further characteristic of the use, according to the invention, of compounds of formula I is the purification step for the compounds of formula Ia, which follows the nucleophilic aromatic substitution, which purification step offers great advantages for industrial-scale processes because complicated separation and purification steps can be avoided and the outlay in terms of apparatus can be reduced.

For that purpose, the reaction mixture rendered aqueous-organic following the nucleophilic aromatic substitution reaction or obtained in that form from a phase transfer-catalysed reaction procedure is adjusted to an acidic pH range of from 1 to 5 with aqueous acid, that acidic reaction mixture is optionally worked-up reductively, and the product is extracted with organic solvents, such as e.g. aromatic hydrocarbons, for example toluene, or ethers, for example THF or dioxane, and the product taken up in the organic phase is optionally re-isolated with an aqueous strong base, preferably in the pH range of from 12 to 14, such as e.g. an alkali metal hydroxide. The compound of formula Ia is thus obtained in the form of a salt in an aqueous solution e.g. as an alkali metal, alkaline earth metal or ammonium salt (Example P6).

Suitable reducing agents for the reductive working-up of resulting di- and poly-sulfides are, for example, diborane, hydrazine and phosphines, which are used in sub-stoichiometric amounts, in equimolar amounts or in a slight excess of from 5 to 15 mol %, based on the compound of formula I used.

Suitable reducing agents are also borohydrides, which are advantageously used in sub-stoichiometric amounts of, for example, from 0.1 to 0.2 molar equivalent, based on the compound of formula I used.

The reductive working-up is carried out at reaction temperatures of from 0° to 80° C., preferably from 10° to 40° C.

In an especially preferred variant of the use according to the invention of compounds of formula I, the nucleophilic aromatic substitution reaction in the compound of formula I is carried out using sodium disulfide, prepared in situ from an equimolar mixture of elemental sulfur and sodium sulfide, in 2-methoxyethanol or N,N-dimethylformamide (DMF) as solvent at a reaction temperature of from 80° to 100° C. for 1 hour and, after the addition of toluene and water, adjustment of the reaction mixture with acid to a pH range of from 1 to 5, extraction of the compound of formula Ia with toluene and then optionally back-extraction of the compound of formula Ia from the toluene phase with an aqueous strong base.

As acid for adjusting the reaction mixture to a pH range of from 1 to 5 there comes into consideration especially an aqueous solution of a mineral acid, such as e.g. sulfuric or hydrochloric acid.

As aqueous strong base for the back-extraction of the compound of formula Ia (in the form of the salt) from the organic phase there comes into consideration especially an aqueous solution of a hydroxide, such as e.g. an alkali metal hydroxide, for example sodium hydroxide solution, with preference being given to the use of a 30% sodium hydroxide solution.

The desired target compound of formula Ia is then in the form of a salt dissolved in water, which can readily be separated out by concentration of the water phase.

The yields of isolated product of formula Ia from the halogen-sulfide exchange reaction are generally >90% of theory (depending on the solvent used, the amount and ratio of alkali metal sulfide/sulfur, the nature and purity of the halide starting material, the duration of the reaction and the method of working-up) with the final product having a purity of >99%.

The present invention relates also to the use of compounds of formula III in the preparation of 7-thio-3H-isobenzofuran-1-one derivatives of formula Ia

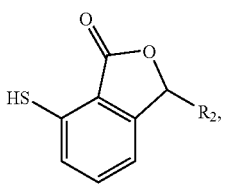

(Ia)

wherein $R_2$ is hydrogen, $C_1$-$C_4$alkyl or $C_1$-$C_4$haloalkyl, wherein a compound of formula III

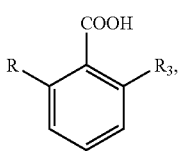

(III)

wherein R is halogen, $R_1S(O)_2$ or $(R_1)_2NC(X)O$; $R_1$ is $C_1$-$C_8$alkyl, aryl-$C_1$-$C_8$alkyl, $C_1$-$C_8$-haloalkyl or aryl; X is O or S; and $R_3$ is $C_1$-$C_5$alkyl or $C_1$-$C_5$haloalkyl, is subjected to benzylic lactonisation in the ortho-position alkyl chain $R_3$ in the presence of a free-radical initiator and a halogenating agent, yielding a compound of formula I

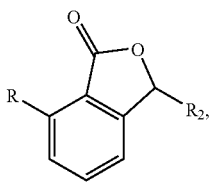

(I)

wherein R and $R_2$ are as defined above, which compound is then reacted at elevated reaction temperature in the presence of sulfur in a nucleophilic aromatic substitution reaction with an alkali metal sulfide, disulfide or polysulfide of formula X $$M_2S_q \qquad (X),$$

wherein M is an alkali metal or hydrogen, and q is 1, 2 or a fractional number from 1 to 7, with the proviso that at least one M is an alkali metal (halogen-sulfide exchange), and optionally, when a reagent of formula X wherein q>1 is used, is worked up reductively and, after the reaction mixture has been rendered acidic, the desired target compound of formula Ia is isolated therefrom and optionally re-isolated in the form of the salt using a strongly basic aqueous solution.

For the use of compounds of formula III in the preparation of compounds of formula Ia, the preferred meanings are the same as those already given above.

The process according to the invention differs from known processes in that:

1) reduction of a nitro compound is not necessary and therefore there is no formation of hydroxylamine, which would adversely affect the thermal safety, 2) there is no reaction with butyllithium, which is expensive and unfavourable for process safety, as described, e.g. in Monatsh. Chem. 123(12), 1125 (1992), 3) the number of toxic starting compounds and reagents is reduced (only CO in Step (2) and the halogenating reagents in Step (3) are toxic), 4) readily accessible and inexpensive starting compounds are used, 5) the lactonisation is achieved in a single step and in high yields, 6) the reaction sequence to obtain the desired target compound of formula I is reduced by one reaction step, 7) in respect of Steps (1) and (2) (diazotisation and carbonylation), the reaction can be designed as a one-pot reaction, 8) the method of working-up is simple and effective, 9) the number of volatile, unpleasant-smelling, toxic waste products is reduced, and 10) the overall yields are higher, simultaneously combined with a high degree of product purity, e.g. in respect of the target compound of formula Ia.

The advantages of the present process compared with known processes are accordingly:

1) its particular suitability for industrial-scale applications with a substantially better waste outcome, e.g. in respect of volatile, sulfur-containing byproducts when using xanthogenates, as in e.g. Pest. Manag Sci. 57, 205-224 (2001), and the small amount of disulfides formed, 2) the high thermal safety of the process, 3) the great variety in its reaction media and reaction conditions, 4) its avoidance of complicated separation and purification steps, 5) the possibility of using the formed diazonium salt of formula II further directly in a one-pot process without changing the solvent, thus reducing solvent wastes and the outlay in terms of apparatus, 6) the high volumetric concentration of the reactants, 7) its high product yields and product purities, 8) its large number of suitable palladium catalysts, 9) its use of catalysts that are either commercially available or can be prepared readily in situ from commercial palladium salts, such as e.g. palladium(II) chloride solution (20%), and the appropriate ligands, and 10) its reproducibility.

The 7-thio-3H-isobenzofuran-1-one derivatives prepared according to the invention are used especially as intermediates in the preparation of 7-[(4,6-dimethoxy-pyrimidin-2-yl)thio]-3-methyl-3H-isobenzofuran-1-one by reacting 7-thio-3-methyl-3H-isobenzofuran-1-one of formula Ia

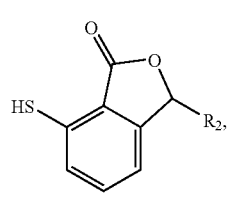

(Ia)

wherein R$_2$ is methyl, advantageously in an inert organic solvent, such as e.g. an ether, ketone, nitrile or amide, for example tetrahydrofuran, butanone, acetonitrile or N,N-dimethylformamide (DMF), at temperatures of from 0 to 160° C., with a compound of formula VI

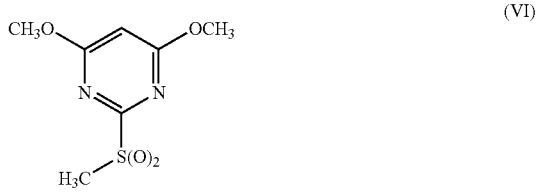

as described, for example, in EP-B-0 447 506.

The following Examples illustrate the process according to the invention further.

EXAMPLE P1

Preparation of 2-chloro-6-ethyl-benzoic acid 3.60 g (21.2 mmol) of 2-chloro-6-ethylaniline and 2.70 g (26.5 mmol) of sulfuric acid (96%) in 100 ml of acetic acid are introduced into a reaction vessel and the clear, colourless solution is cooled to 10° C. At that temperature, a solution of 1.46 g (21.2 mmol) of sodium nitrite in 8 ml of water is slowly added in the course of 15 minutes. When a diazo colour test, e.g. using dimethylaniline-coated indicator paper, is positive and a colour spot test, e.g. using KI indicator paper moistened with 1N aqueous hydrochloric acid solution, is negative, the reaction mixture is transferred to a glass autoclave and rinsed with 20 ml of acetic acid. The autoclave is flushed out three times with nitrogen at a temperature of 10° C. and then flushed out three times with CO at 7° C. 55 mg of Pd$_2$(dba)$_3$.CHCl$_3$ (0.053 mmol) in 2 ml of acetic acid are then metered in using a cannula, a CO pressure of 6.3 bar is applied and the reaction mixture is stirred overnight at 20° C.

After the pressure has been released, 25 ml of a 1N aqueous sodium hydroxide solution are added and the resulting suspension is filtered. The orange-brown filtrate is adjusted to pH 2 with sulfuric acid and extracted three times with 40 ml of toluene each time. The combined organic phases are washed three times with 40 ml of water each time, dried over sodium sulfate and concentrated by evaporation under reduced pressure using a rotary evaporator. The crude yield is 3.24 g with a target compound content of 70% according to HPLC. The pure yield of the desired target compound after purification by means of vacuum distillation (b.p. 130-135° C./0.01 mbar) is 2.24 g (57% of theory).

EXAMPLE P2

Preparation of 2-chloro-6-ethyl-benzoic acid 3.60 g (21.2 mmol) of 2-chloro-6-ethylaniline in 60 ml of acetic acid is introduced into a reaction vessel and the clear, colourless solution is cooled to 6° C. At that temperature, 3.64 g (22.7 mmol) of a 43% aqueous sodium nitrite solution are added and then, in the course of 15 minutes, a solution of 4.32 g (42.4 mmol) of sulfuric acid (96%) in 7 ml of acetic acid is added dropwise. The resulting dark-red solution is then stirred for 30 minutes. When a diazo colour test, for example using dimethylaniline-coated indicator paper, is positive and a colour spot test, e.g. using KI indicator paper moistened with aqueous 1N hydrochloric acid solution, is negative, 15 mg of sulfamic acid are added and then, at a temperature of 10° C., 8.7 ml (91.6 mmol) of acetic anhydride are added. The reaction mixture is then transferred to a glass autoclave and rinsed with 20 ml of acetic acid. At a temperature of 20° C. the autoclave is flushed out three times with nitrogen and then flushed out three times with CO. 220 mg of Pd$_2$(dba)$_3$.CHCl$_3$ (0.212 mmol) in 5 ml of acetic acid are then metered in using a cannula at a CO pressure of 1 bar, then a CO pressure of 8 bar is applied and the reaction mixture is stirred overnight at 45° C. When the pressure has been released, the resulting suspension is filtered and the acetic acid filtrate is concentrated by evaporation under reduced pressure using a rotary evaporator; 1M aqueous hydrochloric acid solution is added to the organic phase that remains and extraction is carried out three times with toluene. The combined organic phases are evaporated under reduced pressure using a rotary evaporator, yielding 4.43 g of crude product with a target compound content of 75% according to HPLC. Purification by means of vacuum distillation (b.p. 130-135° C./0.01 mbar) yields 3.31 g (yield 85% of theory) of the desired target compound.

EXAMPLE P3

Preparation of 2-chloro-6-ethyl-benzoic acid 3.60 g (21.2 mmol) of 2-chloro-6-ethylaniline in 24 ml of acetic acid are introduced into a reaction vessel and the clear, colourless solution is cooled to 11° C. At that temperature, 3.25 g (31.8 mmol) of sulfuric acid (96%) are added and then, in the course of 15 minutes, 3.64 g (22.7 mmol) of a 43% aqueous sodium nitrite solution are added. The resulting dark-red solution is then stirred for 30 minutes. When a diazo colour test, e.g. using dimethylaniline-coated indicator paper, is positive and a colour spot test, e.g. using KI indicator paper moistened with aqueous 1N hydrochloric acid solution, is negative, 15 mg of sulfamic acid are added and then, at a temperature of 10° C., 8.7 ml (91.6 mmol) of acetic anhydride are added. The reaction mixture is then transferred to a glass autoclave and rinsed with 6 ml of acetic acid. At a temperature of 20° C. the autoclave is flushed out three times with nitrogen and then three times with CO. 220 mg of Pd$_2$(dba)$_3$.CHCl$_3$ (0.212 mmol) in 3 ml of acetic acid are metered in using a cannula at a CO pressure of 1 bar, then a CO pressure of 8 bar is applied and the reaction mixture is stirred for 5 hours at 45° C.

When the pressure has been released, the resulting suspension is filtered and the acetic acid filtrate is concentrated by evaporation under reduced pressure using a rotary evaporator; 1M aqueous hydrochloric acid solution is added to the organic phase that remains and extraction is carried out three times with toluene. The combined organic phases are evaporated under reduced pressure using a rotary evaporator, yielding 3.72 g of crude product with a target compound content of 75% according to HPLC. Purification by means of vacuum distillation (b.p. 130-135° C./0.01 mbar) yields 2.12 g (yield 55% of theory) of the desired target compound.

EXAMPLE P4

Preparation of 7-chloro-3-methyl-3H-isobenzofuran-1-one 5.00 g (0.027 mol) of 2-chloro-6-ethylbenzoic acid in 120 ml of chlorobenzene are introduced into a reaction vessel and heated to 90° C. 0.1 g of α,α'-azoisobutyronitrile is then added, followed by 5.04 g (0.03154 mol) of bromine in 25 ml of chlorobenzene, which is metered in the course of 10 minutes. The reaction mixture is then stirred for 1 hour at 90° C. to complete the reaction. After the reaction mixture has cooled to 20° C., it is washed with 50 ml of sodium thiosulfate solution (0.1 mol), the organic phase is dried over sodium sulfate and the solvent evaporated off under reduced pressure using a rotary evaporator. The desired target compound is obtained in a yield of 6.1 g and a purity of about 74% (corresponding to 90% of theory).

EXAMPLE P5

Preparation of
7-thio-3-methyl-3H-isobenzofuran-1-one 5.70 g of 7-chloro-3-methyl-3H-isobenzofuran-1-one is introduced into a reaction vessel together with 1.30 g of sulfur and 5.40 g of sodium sulfide in 30 ml of DMF, the mixture is heated to 90° C. and left to react for 1 hour. Once all the starting material has reacted, the reaction mixture is cooled to 20° C., 50 ml of toluene and 30 ml of water are added and the mixture is adjusted to a pH of 3. The resulting suspension is filtered over Hyflo and the organic phase is separated from the two-phase mother liquor. The organic phase is then extracted with 50 ml of aqueous sodium hydroxide solution. The desired target compound is obtained in the form of the sodium salt in a yield of 4.3 g (80% of theory).

EXAMPLE P6

Preparation of
7-thio-3-methyl-3H-isobenzofuran-1-one 15 g of 2-methoxyethanol are introduced into a 200 ml reaction vessel and, together with 1.9 g of 7-chloro-3-methyl-3H-isobenzofuran-1-one, 1.8 g of sodium sulfide and 0.43 g of sulfur, are heated to 110° C. After 6 hours' reaction time, the mixture is cooled to 20° C. and a mixture of 20 ml of water and 1 ml of 12% sodium borohydride solution is added. After being left to stand for 5 minutes, 20 ml of toluene are added and the pH value of the reaction mixture is adjusted to from 1 to 1.5 with hydrochloric acid. The organic phase is separated off and then extraction is carried out twice with 10 ml of aqueous sodium hydroxide solution. The desired target compound is obtained in the form of the sodium salt in a yield of 80% as a 2.8% aqueous solution.

EXAMPLE P7

Preparation of
7-thio-3-methyl-3H-isobenzofuran-1-one

The reaction is started analogously to the manner described above in Example P5. Working-up of the desired target compound is carried out reductively by means of extraction from an acid medium, separation of the organic phase and treatment thereof with 5 mol % triphenylphosphine. Back-extraction of the reaction mixture with 25 ml of sodium hydroxide solution yields the desired target compound in the form of the sodium salt in an aqueous solution in a yield of 82%.

What is claimed is:

1. A compound of formula I

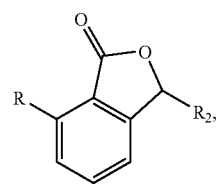

Wherein:
R is bromine or $R_1S(O)_2$
$R_1$ is $C_1$-$C_8$alkyl, $C_1$-$C_8$-haloalkyl, aryl-$C_1$-$C_8$alkyl or aryl; and
$R_2$ is methyl.

* * * * *